United States Patent [19]

Ladika et al.

[11] Patent Number: 5,391,634
[45] Date of Patent: Feb. 21, 1995

[54] OPTICALLY-ACTIVE, AMPHIPHILIC, WATER-SOLUBLE FREE-RADICAL ADDITION COPOLYMERS AND THEIR USE IN THE RESOLUTION OF RACEMIC MIXTURES

[75] Inventors: Mladen Ladika; Thomas E. Fisk, both of Midland, Mich.

[73] Assignee: The Dow Chemical Company, Midland, Mich.

[21] Appl. No.: 184,802

[22] Filed: Jan. 21, 1994

Related U.S. Application Data

[63] Continuation-in-part of Ser. No. 67,776, May 26, 1993, abandoned.

[51] Int. Cl.⁶ .......................................... C08F 278/02
[52] U.S. Cl. .......................... 525/328.2; 525/330.2; 525/330.4; 525/327.3; 525/328.8; 526/287; 526/286; 526/284; 526/292.2; 562/401; 562/402; 564/302; 564/303
[58] Field of Search .............. 525/328.2, 330.4, 330.2; 526/286, 287; 562/401, 402; 564/302, 303; 424/78.18, 78.35

[56] References Cited

U.S. PATENT DOCUMENTS

| | | | |
|---|---|---|---|
| 4,138,542 | 2/1979 | Siegel et al. | 526/305 |
| 4,864,031 | 9/1989 | Zbaida et al. | 548/339.1 |
| 4,914,159 | 4/1990 | Bömer et al. | 525/328.2 |
| 4,931,525 | 6/1990 | Schwartz et al. | 526/305 |
| 5,252,673 | 10/1993 | Hirano et al. | 525/183 |
| 5,280,093 | 1/1994 | Jacquier et al. | 526/263 |

OTHER PUBLICATIONS

Sigma Chemical Co., 1993 Biochemicals Catalogue, p. 676.
Albert L. Lehninger, Biochemistry, Worth Publishers, Inc., New York, 1975, Chap. 4, pp. 73–75.
S. D'Antone et al., "Chiral Functional Polymers as Catalysts in Phase Transfer Reactions," *Reactive Polymers*, 3 (1985) pp. 107–125.
R. Majumdar et al, "Spectroscopic Characterization and Chiroptical Properties of the Copolymers of (−)--Methyl Acrylate and (−)-Menthyl Methacrylate with Styrene," *Makromol. Chem.* 181, pp. 201–214 (1980).
G. Zabay, *Biochemistry*, Addison-Wesley Publishing Company, Reading, 1983, Chap. 2, pp. 40–43.

*Primary Examiner*—Mark Nagumo
*Attorney, Agent, or Firm*—Craig E. Mixan

[57] ABSTRACT

Optically-active, amphiphilic, free-radical addition copolymers having an optically-active hydrophobic portion and an ionic hydrophilic portion are effective resolving agents. This utility is based on a unique combination of properties, viz., water solubility, chirality and amphiphilicity, i.e., having a dual hydrophobic and hydrophilic nature.

5 Claims, No Drawings

OPTICALLY-ACTIVE, AMPHIPHILIC, WATER-SOLUBLE FREE-RADICAL ADDITION COPOLYMERS AND THEIR USE IN THE RESOLUTION OF RACEMIC MIXTURES

RELATED U.S. APPLICATION DATA

Continuation-in-part of Ser. No. 08/067,776, May 26, 1993 now abandoned.

FIELD OF THE INVENTION

The present invention concerns optically-active, water-soluble free-radical, addition copolymers of ethylenically unsaturated monomers having a hydrophobic component which contains a chiral moiety and a hydrophilic component which contains an ionic or ionizable moiety. Such compositions are useful for the resolution of racemic mixtures.

BACKGROUND OF THE INVENTION

The separation of enantiomers continues to be a considerable challenge in preparative chemistry, particularly on an industrial scale.

The majority of currently used methods for the resolution of racemic mixtures are based on the diastereomeric interactions of the individual enantiomers of the racemic mixture with an optically-active resolving agent. For instance, by chemically reacting a racemate with an optically-active resolving agent, a pair of diastereomers are produced which can be separated on the basis of their different physical properties. Rather than forming discrete compounds (diastereomers) from which the enantiomers must be recovered by subsequent chemical reactions, it is also possible to make use of diastereomeric complexes or reversible interactions to achieve resolutions. Such an approach forms the basis of chromatographic separations involving either the use of a chiral stationary phase or of a chiral additive to the mobile phase; see I. W. Wainer, *Chromatography Forum*, 1, 55 (1986).

Certain chiral functional homopolymers, e.g., poly(acrylo)-aminoacids, are useful as effective crystallization inhibitors of one enantiomer in the resolution of racemic mixtures that crystallize in the form of conglomerates; see U.S. Pat. No. 4,864,031. Chemical yields, however, are relatively low when high enantiomeric excesses are desired. Other optically-active functional polymers, including optically-active polymers bearing polar non-ionic oligoether groups or cationic quaternary ammonium groups, have been investigated by S. D'Antone et al., in *Reactive Polymers*, 3, (1985), pages 107–125.

SUMMARY OF THE INVENTION

We have now found that optically-active, amphiphilic, free-radical addition copolymers are useful for the resolution of racemic mixtures. The present invention concerns a process for the resolution of a racemic mixture or a partially resolved mixture of enantiomers which is characterized by contacting the mixture with an optically-active, amphiphilic, water-soluble, free-radical addition copolymer, and separating the enantiomers on the basis of their diastereomeric or selective interactions with the chiral copolymer. More particularly, the present invention is characterized by contacting the racemic mixture with an optically-active, amphiphilic, water-soluble, free-radical addition copolymer which is comprised of (i) a hydrophobic component having a chiral moiety, and (ii) a hydrophilic component having an ionic or ionizable moiety. The optically-active, amphiphilic, water-soluble copolymers are preferably comprised of:

25–80 weight percent of a hydrophilic component having an ionic or an ionizable functionality;

3–70 weight percent of a hydrophobic component having a chiral functionality; and 0–62 weight percent of an achiral hydrophobic component.

Separation of enantiomers can be accomplished by utilizing these materials in such diverse techniques as dialysis, ultrafiltration and selective crystallization.

The present invention also concerns the novel optically-active, amphiphilic, water-soluble free-radical addition copolymers of ethylenically unsaturated monomers comprising (i) a hydrophobic component having a chiral moiety, and (ii) a hydrophilic component having an anionic group or a cationic sulfonium group. The optically-active, amphiphilic, water-soluble addition copolymers are preferably comprised of:

25–80 weight percent of a hydrophilic component having an anionic functionality or a cationic sulfonium functionality;

3–70 weight percent of a hydrophobic component having a chiral functionality; and 0–62 weight percent of an achiral hydrophobic component.

DETAILED DESCRIPTION OF THE INVENTION

By addition copolymer is meant a copolymer formed by direct free-radical initiated addition or combination of at least two different ethylenically unsaturated monomer molecules with one another.

The copolymeric compositions of the present invention are characterized by their unique combination of features, viz., water solubility, optical activity and amphiphilic character, i.e., having both a hydrophilic and a hydrophobic nature. Thus, these polymeric compositions are comprised of a hydrophobic component bearing an chiral moiety and a hydrophilic component bearing an ionic or ionizable moiety. These compositions also can include an achiral, hydrophobic component which optionally contains polymerizable groups which enable further crosslinking.

The addition copolymers of the present invention require a hydrophilic component with ionic or ionizable functionality. The ionic functionality may be either anionic or cationic in nature. Suitable cationic species include substituted ammonium, phosphonium or sulfonium groups which are substituted with straight-chained or branched-chained alkyl groups of from 1 to 4 carbon atoms inclusive (R). Preferred cationic groups are substituted ammonium [$-N^{\oplus}R_3$] and substituted sulfonium [$-S^{\oplus}R_2$] groups. R is preferably methyl. Suitable anionic species include carboxylate, sulfonate and phosphonate groups. Preferred anionic groups are sulfonate [$-SO_3^{\ominus}$] and carboxylate [$-CO_2^{\ominus}$].

The addition copolymers must be at least partially soluble in water. Water solubility is based upon the polar interactions at the ionic sites and is dependent on the number, position and frequency of such sites. For the purposes of this invention, the addition copolymers are considered to be of sufficient water solubility if the ionic or ionizable functionalities, e.g., [$-CO_2^{\oplus}$] or [$-N^{\ominus}R_3$] groups, comprise at least 5 weight percent of the composition.

The hydrophilic component is introduced into the addition copolymer by copolymerization with an ethylenically unsaturated monomer which already contains the ionic species or which contains a precursor functionality which can be readily converted into the ionic species. Examples of precursor groups which can be readily converted to cationic species are reactive halides which can react with neutral nucleophiles to produce cationic groups. Preferred cationic precursor functionalities are pendent benzyl halides which are capable of reacting, for example, with ammonia or dimethyl sulfide to produce the unsubstituted ammonium and dimethyl sulfonium cations respectively, e.g., or are amines or sulfides which are capable of reacting with an alkyl halide to produce a substituted ammonium or sulfonium cation, e.g.,

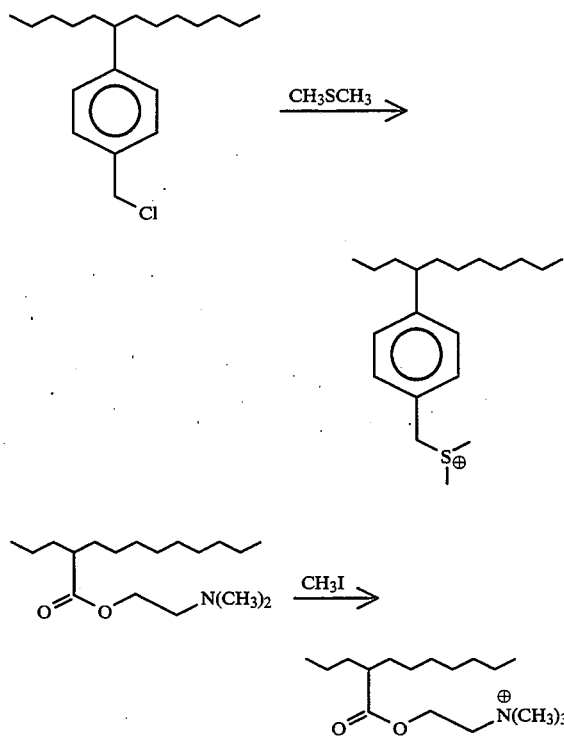

Examples of precursor groups which can be readily converted to anionic species are the corresponding acid derivatives which can be hydrolyzed under alkaline conditions to the carboxylate, sulfonate or phosphonate anions and reactive aliphatic halides, such as pendent benzyl halides, which can react with sulfites or phosphites to produce anionic sulfonates and phosphonates. Preferred anionic precursor functionalities are the carboxylic acid esters and sulfonic acid esters which are readily hydrolyzed under alkaline conditions to the preferred carboxylate and sulfonate anions.

The hydrophilic component containing either the ionic group or a synthetic precursor to the ionic group is preferentially incorporated into the addition copolymer by copolymerization with ethylenically unsaturated monomers containing the desired functionality. The preferred unsaturated monomers are of the styrenic or of the acrylic or methacrylic type. The acrylic and methacrylic type monomers are inclusive of the corresponding acids, esters and amides. Suitable styrenic monomers include, for example, styrene sulfonic acid sodium salt, vinylbenzoic acid and vinylbenzylchloride (VBC). Suitable acrylic or methacrylic monomers include, for example, methacrylic acid, 2-acrylamido-2-methyl-1-propanesulfonic acid (AMPS), 2-acrylamido-glycolic acid, and 2-(dimethylamino)ethyl methacrylate.

Alternatively, a portion of the aromatic-rings in unsubstituted polystyrene may be directly functionalized, e.g., by sulfonation or by chloromethylation followed by amination.

The hydrophilic monomeric component generally comprises from 25 to 80 weight percent of the total monomer employed to produce the desired addition copolymer, preferably from 30 to 60 weight percent.

The addition copolymers also require a hydrophobic component; it is this component which carries the chiral functionality. The hydrophobic component is preferentially incorporated into the addition copolymer by copolymerization with an ethylenically unsaturated monomer, preferably an optically-active monomer. Suitable optically-active ethylenically unsaturated monomers include the following: chiral alkenes, such as β-pinene and limonene, and substituted chiral alkenes, such as 1-penten-3-ol; chiral vinyl ethers and esters, such as vinyl sec-butyl ether and vinyl 2-alkoxy- or 2-aryloxy-propionates; and chiral esters and amides of acrylic, methacrylic and vinylacetic acids, such as menthyl methacrylate, bornyl acrylate, cholesteryl vinylacetate and N-(1-phenylethyl) methacrylamide. The preferred chiral alkenes are the optically-active esters and amides of acrylic and methacrylic acids.

These optically-active unsaturated monomers can be produced by routine methods well known to those of ordinary skill in the art. For example, the preferred optically-active esters and amides of acrylic and methacrylic acids can be prepared by the reaction of the appropriate unsaturated acid chloride with an optically-active alcohol or amine. Preferred chiral alcohols include terpene-derived alcohols like menthol, borneol and α-terpineol, steroid-derived alcohols like cholesterol, and secondary alcohols like α-methyl benzyl alcohol. Preferred chiral amines include primary amines of secondary alkyl groups like G-methyl benzyl amine, 2-amino-1-alkanols derived from α-aminoacids like alaninol, and primary amines derived from terpenes like bornylamine.

The hydrophobic monomeric component generally comprises from 3 to 70 weight percent of the total monomer employed to produce the desired addition copolymer, preferably from 10 to 50 weight percent.

The addition copolymers may also include an achiral, hydrophobic component. Optionally, the achiral, hydrophobic component can contain polymerizable groups which allow a limited amount of crosslinking. Too much crosslinking may adversely affect the water solubility of the resulting addition copolymer. The achiral hydrophobic component is preferentially incorporated into the addition copolymer by copolymerization with achiral ethylenically unsaturated monomers. Suitable achiral unsaturated monomers include the following: alkenes, such as propylene and butadiene; styrene and substituted styrenes, such as t-butylstyrene, α-methyl-styrene and divinylbenzene; ester and amide derivatives of acrylic and methacrylic acids, such as ethyl acrylate, acrylamide, methyl methacrylate, lauryl methacrylate, allyl methacrylate and 2-hydroxyethyl methacrylate; vinyl ethers and esters, such as alkyl vinyl ethers and vinyl alkanoates; and vinyl nitriles, such as acrylonitrile.

The hydrophobic achiral monomeric component generally comprises from 0 to 62 weight percent of the total monomer employed to produce the desired addition copolymer, preferably from 15 to 55 weight percent. Any vinyl-addition crosslinkable component, e.g., allyl methacrylate, is limited to 10 weight percent or less of the monomer employed to produce the desired addition copolymer, preferably less than 3 weight percent.

The addition copolymers of the present invention are prepared by the free-radical addition copolymerization of the appropriate components, e.g., a hydrophilic component which contains an ionic functionality or a precursor which can be readily converted into an ionic functionality, a hydrophobic component which preferably contains the chiral functionality and optionally an achiral hydrophobic component. Such copolymerizations are typically achieved by those routine procedures well known to those skilled in the art. For example, for terminally unsaturated monomers which are the preferred starting materials for the addition copolymers of the present invention, copolymerization is accomplished by free radical polymerization of the vinyl groups of the monomers. Thus, for example, the monomeric components are contacted together under an inert atmosphere with a free radical initiator in the presence of an inert organic solvent under conditions which afford polymerization, typically elevated temperatures and a nitrogen atmosphere. If a monomer which serves as a precursor to the ionic functionality was originally employed in the polymerization, the resulting reaction mixture is further contacted with the appropriate reagent under conditions which convert the precursor into the ionic functionality. The desired addition copolymers are isolated by conventional procedures. Often it is most convenient to isolate the product as an aqueous solution.

The following examples illustrate the preparation of a representative number of chiral, water-soluble, free-radical addition copolymers of the present invention. All specific rotations ($[\alpha]_D^{25}$) were determined on water solutions of the polymers by measuring the rotation of the plane of polarized light of the aqueous solution at a wavelength of 589 nanometers (nm) and at a temperature of 25° C. and by dividing the observed rotation by the path length of the cell in decimeters and the concentration of the sample in g/100 mL.

EXAMPLE 1

Sulfonium-Ion Containing Addition Copolymers Based on Menthyl Methacrylate

A 500 milliliter (mL) three-necked round-bottom flask was equipped with a nitrogen inlet, a reflux condenser connected to an oil bubbler with a nitrogen outlet, and a magnetic stirring bar. The flask was immersed into an oil bath and a nitrogen atmosphere was established. 2-Butanone (32 mL) was placed into the flask and heated to reflux (temperature of the oil bath = 85°–87° C.). A solution of L-menthyl methacrylate (6.5 grams (g)), methyl methacrylate (28.5 g) vinylbenzylchloride (15.0 g), and VAZO-64 TM ]trademark of DuPont for 2,2'-azobis(2-methyl-propanenitrile)] (1.0 g) in 2-butanone (32 mL) was added dropwise by syringe at a rate of 1 mL/minute (mL/min), while constantly maintaining the nitrogen atmosphere and the reflux. After all of the monomer solution was added, an additional portion of VAZO-64 (0.13 g) was added and stirring at reflux was continued for an additional 90 min. Analysis of the resulting solution on a percentage of solids basis indicated that the conversion of monomers to polymers is about 95 percent.

The above solution of non-ionic polymer in 2-butanone was placed into a 500 mL one-necked round-bottom flask equipped with a reflux condenser and a magnetic stirring bar. Tetrahydrofuran (125 mL) was added to this solution, followed by methyl sulfide (16.5 g; 19.5 mL; 0.265 mol). The resulting mixture was stirred at 35° C. for 1 hour (hr) and at 45° C. for an additional 1 hr. After this, water (190 mL) was very slowly added in small portions over several hours. Organic solvents and unreacted methyl sulfide were removed by rotary-evaporation to give a pale-yellow, transparent, aqueous solution containing about 19 weight percent of the sulfonium-ion containing addition copolymer based on menthyl methacrylate. The $[\alpha]_D^{25}$ for the addition copolymer of Example 1 was −11.3°.

EXAMPLES 2–7

Sulfonium-ion containing addition copolymers based on L-menthyl methacrylate were prepared by procedures comparable to Example 1 (Table I).

TABLE I

Sulfonium-Ion Containing Addition Copolymers Based on L-Menthyl Methacrylate

| EXAMPLE | MONOMERS (WEIGHT %) | | | | | $[\alpha]_D^{25}$ |
|---|---|---|---|---|---|---|
| | MnMA | MMA | VBC | HEMA | AMA | |
| 2 | 13 | 47 | 30 | 10 | — | −12.7 |
| 3 | 13 | 45 | 30 | 10 | 2 | −11.5 |
| 4 | 13 | 37 | 50 | — | — | — |
| 5 | 13 | 15 | 50 | 20 | 2 | — |
| 6 | 3 | 47 | 50 | — | — | −3.1 |
| 7 | 3 | 15 | 50 | 30 | 2 | −2.9 |

MnMa = L-menthyl methacrylate
MMA = methyl methacrylate
VBC = vinylbenzylchloride
HEMA = 2-hydroxyethyl methacrylate
AMA = allyl methacrylate

EXAMPLE 8

Sulfonium-Ion Containing Addition Copolymers Based on (1-Phenyl)ethyl Metharcylamide A 250-mL three-necked round-bottom flask was equipped with a nitrogen inlet, a reflux condenser connected to an oil bubbler with a nitrogen outlet, and a magnetic stirring bar. The flask was immersed into an oil bath and a nitrogen atmosphere was established. 2-Butanone (16 mL) was placed into the flask and heated to reflux (temperature of the oil bath = 85°–87° C.). A solution of L-(1-phenyl)ethyl methacrylamide (17.5 g), vinylbenzylchloride (7.5 g), and VAZO-64 (0.5 g) in 2-butanone (16 mL) was added dropwise by syringe at a rate of 1 mL/min, while constantly maintaining the nitrogen atmosphere and reflux. After all of the monomer solution was added, an additional portion of VAZO-64 (0.06 g) was added and stirring at reflux was continued for an additional 90 min. The majority of 2-butanone was then evaporated off and hexane (100 mL) was added to the remaining mixture to precipitate the non-ionic polymer. This solid was washed with hexane (5 × 50 mL), collected by filtration on a Buchner funnel, and dried in vacuo to give a light-tan powder. Yield = 87 percent. $^1$H NMR (CDCl$_3$): δ7.0–7.8 (aryl), 4.7–5.2 (CH—NH), 4.50 (CH$_2$Cl), 2.8 (CH-aryl), 1.27 (CH$_3$—C-aryl), 0.89 (CH$_3$), 0.4–1.8 (backbone CH$_2$).

The non-ionic polymer (5.0 g) and tetrahydrofuran (20 mL) were introduced into a 100 mL one-necked round-bottom flask equipped with a reflux condenser and a magnetic stirring bar to give a clear solution. Methyl sulfide (2.0 mL) was then added and the resulting mixture was stirred at 45° C. for two hr. After this, water (20 mL) was very slowly added in small portions over several hours. Organic solvents and unreacted methyl sulfide were removed by rotary-evaporation to give a pale-yellow, transparent aqueous solution containing about 20 weight percent of the sulfonium-ion containing addition copolymer based on (1-phenyl)ethyl methacrylamide.

EXAMPLES 9–12

Sulfonium-ion containing addition copolymers based on L-(1-phenyl)ethyl methacrylamide were prepared by procedures comparable to Example 8 (Table II).

TABLE II

Sulfonium-Ion Containing Addition Copolymers Based on L-(1-Phenyl)ethyl Methacrylamide

| EXAMPLE | MONOMERS (WEIGHT %) | | | | |
|---|---|---|---|---|---|
|  | PMA | MMA | LMA | VBC | HEMA |
| 9 | 13 | 57 | — | 30 | — |
| 10 | 13 | 47 | — | 30 | 10 |
| 11 | 13 | 37 | 20 | 30 | — |
| 12 | 50 | 20 | — | 30 | — |

PMA = L-(1-phenyl)ethyl methacrylamide
MMA = methyl methacrylate
LMA = lauryl methacrylate
VBC = vinyl benzyl chloride
HEMA = 2-hydroxyethyl methacrylate The $[\alpha]_D^{25}$ for the addition copolymer of Example 10 was $-8.7°$.

EXAMPLE 13

Ammonium-Ion Containing Addition Copolymers Based on Menthyl Methacrylate

A 500 mL three-necked round-bottom flask was equipped with a nitrogen inlet, a reflux condenser connected to an oil bubbler with a nitrogen outlet, and a magnetic stirring bar. The flask was immersed into an oil bath and a nitrogen atmosphere was established. 2-Butanone (32 mL) was placed into the flask and heated to reflux (temperature of the oil bath = 85°–87° C.). A solution of L-menthyl methacrylate (6.5 g), methyl methacrylate (23.5 g), 2-(dimethylamino)ethyl methacrylate (20.0 g), and VAZO-64 (1.0 g) in 2-butanone (32 mL) was added dropwise by syringe at a rate of 1 mL/min, while constantly maintaining the nitrogen atmosphere and reflux. After all of the monomer solution was added, an additional portion of VAZO-64 (0.13 g) was added and stirring at reflux was continued for an additional 90 min. Analysis of the resulting solution on a percentage of solids basis indicated that the conversion of monomers to polymers is about 95 percent.

The above solution of non-ionic polymer in 2-butanone was placed into a 1000 mL one-necked round-bottom flask equipped with a reflux condenser and a magnetic stirring bar. Tetrahydrofuran (250 mL) was added to this solution, followed by iodomethane (24 mL). The conversion was very fast and a considerable amount of precipitate formed instantaneously. The resulting mixture was stirred at 45° C. for one hr. After this, water (150 mL) was added and organic solvents and unreacted iodomethane were removed by rotary-evaporation to give a light-red, transparent, viscous oil (about 24 weight percent polymer in water). This material was further diluted with water to give a clear orange aqueous solution (4.8 weight percent polymer).

EXAMPLE 14 and 15

Ammonium-ion containing addition copolymers based on L-menthyl methacrylate were prepared by procedures comparable to Example 13 (Table III).

TABLE III

Ammonium-Ion Containing Addition Copolymers Based on L-Menthyl Methacrylate

| EXAMPLE | MONOMERS (WEIGHT %) | | |
|---|---|---|---|
|  | MnMA | MMA | DMAEMA |
| 14 | 13 | 62 | 25 |
| 15 | 13 | 32 | 55 |

MnMA = L-menthyl methacrylate
MMA = methyl methacrylate
DMAEMA = 2-(dimethylamino)ethyl methacrylate

EXAMPLE 16

Sulfonate-Ion Containing Addition Copolymers Based on Menthyl Methacrylate

A 1000 mL five-necked round-bottom flask was equipped with a nitrogen inlet, a reflux condenser connected to an oil bubbler with a nitrogen outlet, five addition funnels, and a magnetic stirring bar. The flask was immersed into an oil bath and a nitrogen atmosphere was established. 2-Propanol (200 g) was placed into the flask and heated to 50° C. Into the five addition funnels were placed:

(a) a solution of 2-acrylamido-2-methylpropanesulfonic acid (AMPS; 60 g) in water (50 g);
(b) a mixture of L-menthyl methacrylate (13.0 g) and methyl methacrylate (27.0 g);
(c) a solution of 2-mercaptoethanol (2-ME; 0.56 g) in water (3.0 g);
(d) a solution of t-butyl hydroperoxide (t-BHP; 0.29 g) in water (3.0 g); and
(e) a solution of sodium formaldehyde sulfoxylate (SFS; 0.15 g) in water (3.0 g).

The solutions were simultaneously added dropwise from the addition funnels over one hour, while constantly maintaining the nitrogen atmosphere and the temperature at 50° C. During the addition, 2-propanol (total additional amount of 145 g) was occasionally added to the reaction mixture in a 1000-mL flask. After all solutions were added, stirring at 50° C. was continued for an additional 2 hr. The reaction mixture was then cooled to ambient temperature and water (350 mL) was slowly added. The resulting solution was transferred into a 2 liter (L) one-necked flask and 2-propanol was removed by rotary-evaporation to give a pale-yellow, transparent aqueous solution containing about 22 weight percent of the desired addition copolymer.

EXAMPLES 17 and 18

Sulfonate-ion containing addition copolymers based on L-menthyl methacrylate were prepared by procedures comparable to Example 16 (Table IV).

TABLE IV

Sulfonate-Ion Containing Addition Copolymers Based on L-Menthyl Methacrylate

| EXAMPLE | MONOMERS (WEIGHT %) | | | | |
|---|---|---|---|---|---|
|  | MnMA | MMA | AMPS | DMAEMA | AMA |
| 17 | 13 | 27 | 50 | 10 | — |

TABLE IV-continued

Sulfonate-Ion Containing Addition Copolymers Based on L-Menthyl Methacrylate

| EXAMPLE | MONOMERS (WEIGHT %) | | | | |
|---|---|---|---|---|---|
| | MnMA | MMA | AMPS | DMAEMA | AMA |
| 18 | 13 | 25 | 50 | 10 | 2 |

MnMA = L-menthyl methacrylate
MMA = methyl methacrylate
AMPS = 2-acrylamido-2-methylpropanesulfonic acid
DMAEMA = 2-(dimethylamino)ethyl methacrylate
AMA = allyl methacrylate

EXAMPLE 19

Sulfonate-Ion Containing Addition Copolymers Based on (1-phenyl)ethyl Methacrylamide A 1L five-necked round-bottom flask was equipped with a nitrogen inlet, a reflux condenser connected to an oil bubbler with a nitrogen outlet, five addition funnels, and a magnetic stirring bar. The flask was immersed into an oil bath and a nitrogen atmosphere was established. 2-Propanol (100 g) was placed into the flask and heated to 50° C. Into the five addition funnels were placed:

(a) a solution of 2-acrylamido-2-methylpropanesulfonic acid (AMPS; 30 g) in water (50 g);
(b) a solution of L-(1-phenyl)ethyl methacrylamide (6.5 g) and methyl methacrylate (13.5 g) in 2-propanol (50 g);
(c) a solution of 2-mercaptoethanol (2-ME; 0.28 g) in water (5.0 g);
(d) a solution of t-butyl hydroperoxide (t-BHP; 0.14 g) in water (5.0 g); and
(e) a solution of sodium formaldehyde sulfoxylate (SFS; 0.075 g) in water (5.0 g).

The solutions were simultaneously added dropwise from the addition funnels over one hour, while constantly maintaining the nitrogen atmosphere and the temperature at 50° C. Stirring at 50° C. was continued for an additional 2 hr. The reaction mixture was then cooled to ambient temperature and water (200 mL) was slowly added. 2-Propanol was removed by rotary-evaporation to give a pale-yellow, transparent aqueous solution containing about 16 weight percent of the desired addition copolymer. The $[\alpha]_D^{25}$ for the addition copolymer of Example 19 was $-10.1°$.

EXAMPLES 20-25

Sulfonate-ion containing addition copolymers based on L-(1-phenyl)ethyl methacrylamide were prepared by procedures comparable to Example 19 (Table V).

TABLE V

Sulfonate-Ion Containing Addition Copolymers Based on L-(1-Phenyl)ethyl Methacrylamide

| EXAMPLE | MONOMERS (WEIGHT %) | | | | | |
|---|---|---|---|---|---|---|
| | PMA | MMA | AMPS | LMA | AMA | NMA |
| 20 | 40 | — | 60 | — | — | — |
| 21 | 13 | 17 | 70 | — | — | — |
| 22 | 13 | 57 | 30 | — | — | — |
| 23 | 13 | 17 | 60 | 10 | — | — |
| 24 | 13 | 25 | 60 | — | 2 | — |
| 25 | 13 | 25 | 60 | — | — | 2 |

PMA = L-(1-phenyl)ethyl methacrylamide
MMA = methyl methacrylate
AMPS = 2-acrylamido-2-methylpropanesulfonic acid
LMA = lauryl methacrylate
AMA = allyl methacrylate
NMA = β-naphthyl methacrylate

EXAMPLE 26

Carboxylate-Ion Containing Addition Copolymers Based on (1-Phenyl)ethyl Methacrylamide A 1 L five-necked round-bottom flask was equipped with a nitrogen inlet, a reflux condenser connected to an oil bubbler with a nitrogen outlet, four addition funnels, and a magnetic stirring bar. The flask was immersed into an oil bath and a nitrogen atmosphere was established. 2-Propanol (100 g) was placed into the flask and heated to 50° C. Into the four addition funnels were placed:

(a) a solution of L-(1-phenyl)ethyl methacrylamide (6.5 g) methyl methacrylate (28.5 g), and methacrylic acid (15.0 g) in 2-propanol (25 g);
(b) a solution of 2-mercaptoethanol (2-ME; 0.28 g) in water (5.0 g);
(c) a solution of t-butyl hydroperoxide (t-BHP; 0.14 g) in water (5.0 g); and
(d) a solution of sodium formaldehyde sulfoxylate (SFS; 0.075 g) in water (5.0 g).

The solutions were simultaneously added dropwise from the addition funnels over one hr, while constantly maintaining the nitrogen atmosphere and the temperature at 50° C. Stirring at 50° C. was continued for an additional 2 hr. The reaction mixture was then cooled to ambient temperature and water (200 mL) was slowly added. After standing overnight at ambient temperature, the polymer separated from the solution in a gelatinous form. The additional portion of 2-propanol (150 g) was added and the reaction mixture was neutralized with NaOH, causing all polymer to dissolve and give a clear solution. 2-Propanol was removed by rotary-evaporation to give a pale-yellow aqueous solution containing about 19 weight percent of the desired addition copolymer. The $[\alpha]_D^{25}$ for the addition copolymer of Example 26 was $-7.0°$.

EXAMPLES 27-29

Carboxylate-ion containing addition copolymers based on L-(1-phenyl)ethyl methacrylamide were prepared by procedures comparable to Example 26 (Table VI).

TABLE VI

Carboxylate-Ion Containing Addition Copolymers Based on L-(1-Phenyl)ethyl Methacrylamide

| EXAMPLE | MONOMERS (WEIGHT %) | | | |
|---|---|---|---|---|
| | PMA | MMA | MAA | AMA |
| 27 | 13 | 55 | 30 | 2 |
| 28 | 50 | 18 | 30 | 2 |
| 29 | 30 | 40 | 30 | — |

PMA = L-(1-phenyl)ethyl methacrylamide
MMA = methyl methacrylate
MAA = methacrylic acid
AMA = allyl methacrylate The optically-active addition copolymers of the present invention are useful for the resolution of racemic mixtures. Such resolutions are typically performed by contacting a racemic mixture or a partially resolved mixture already enriched in one enantiomer with an aqueous solution of the optically-active, amphiphilic, water-soluble copolymer. The addition copolymer can either form a diasteromeric complex with each enantiomer or can preferentially interact with one enantiomer over the other. In either case, the enantiomers can be effectively separated on the basis of their diastereomeric or selective interactions with the chiral polymer. Examples of suitable means for separating the enantiomers include dialysis, ultrafiltration, selective crystallization and chromatography. Preferred methods of separation are ultrafiltration and selective crystallization.

Since the optically-active addition copolymers are water soluble, the racemic mixtures sought to be resolved are preferably themselves soluble in water, at least to the extent of tenths of a weight percent. Thus, while optically-active addition copolymers can be used to separate racemic mixtures of both polar and nonpolar substrates, they are much more effective in resolving polar compounds. Preferred substrates are dipolar or amphoteric compounds like aminoacids and aminoalcohols. Such compounds have appreciable water solubility at both high and low pH.

The ratio of optically-active, amphiphilic copolymer to substrate can effectively range from 0.5/1 to greater than 15/1. In general, the higher the ratio, the greater the discrimination between enantiomers. Beyond a certain ratio, however, little, if any, enhanced resolution is achieved. Optically-active addition copolymer to substrate ratios of about 0.8 to about 5 are usually preferred.

Either the R- or the S- configuration (D- or L- configuration) of an optically-active monomer can be incorporated into the addition copolymer. While it cannot be predicted which enantiomer of the racemic mixture will preferentially interact with the optically-active polymer in a particular resolution process, the result can easily be determined by routine experimentation. Furthermore, both configurations of the optically-active addition copolymer are equivalent in their resolving power so that replacement of one configuration for the other in the polymer, results in the preferential interaction with the other enantiomer of the racemic mixture.

In a typical enantioselective crystallization, a dipolar substrate is dissolved in an aqueous solution of an optically-active addition copolymer and the pH is adjusted to precipitate the enantiomer of a substrate least associated with the optically-active, amphiphilic copolymer. The precipitated enantiomer can be isolated by filtration.

Alternatively, in a typical ultrafiltration, a racemic mixture is dissolved in an aqueous solution of an optically-active addition copolymer and the solution is ultrafiltered through a size-selective membrane which retains polymers. The filtrate is enriched in the enantiomer of a substrate least associated with the optically-active, amphiphilic copolymer. In those cases where enantiomeric enrichment is not great per unit operation, effective resolution can be achieved by multistage operation.

The following examples are illustrative of the resolution process of the present invention.

EXAMPLE A

Resolution by Enantioselective Crystallization

Racemic D,L-cystine (150 milligrams (mg)) was dissolved in 0.13N HCl (9.85 g) and a 22 weight percent solution (5.0 g) of the optically-active addition copolymer of Example 3. The pH of the clear solution was adjusted to 2.30 by the careful addition of 5 percent NaOH solution. The resulting precipitate was washed with deionized water (pH=6.8) and dried under vacuum to give 76.6 mg of white crystals. The $[\alpha]_D^{25}$ of an aqueous solution of the resolved material was 220°±45°, which corresponds to an enantiomeric excess of over 96 percent of the L-isomer.

EXAMPLE B

Resolution by Ultrafiltration

1. An aqueous solution of the copolymer of Example 9 (4.50 g of 13.3 weight percent solution) was added to the solution of racemic (D,L)-tryptophan (100 mg) in 0.01M HCl (1.50 g). The resulting clear mixture was placed into an ultrafiltration cell ("Amicon", Model 8010; cell capacity=10 mL) and filtered through a size-exclusion membrane ("Millipore"-PLAC 090; regenerated cellulose; nominal molecular weight limit NMWL=1000) under 50 psi pressure (compressed air). The clear, colorless filtrate was tested for optical activity using polarimetry. A $[\alpha]_D^{25}$ of −3.17° showed that the filtrate was enriched in (L)-tryptophan [enantiomeric excess of (L)-tryptophan ∼21 percent]. This result was verified by high pressure liquid chromatography (HPLC) using a chiral CROWNPAK CR (+) TM (Trademark of Daicel Chemical Industries) column.

2. An aqueous solution of the copolymer of Example 9 (4.50 g of 13.3 weight percent solution) was added to the solution of racemic (R,S)-4-amino-5-hexenoic acid (100 mg) in water (1.50 g). The resulting clear mixture was ultrafiltered according to the procedure described in Example B-1. A $[\alpha]_D^{25}$ of −1.26° showed that the sample was enriched in (R)-isomer [enantiomeric excess of (R)-isomer ∼10 percent].

3. An aqueous solution of the copolymer of Example 19 (4.50 g of 15.7 weight percent solution) was added to the solution of racemic (D,L)-tryptophan (100 mg) in 0.01M HCl (1.50 g). The resulting clear mixture was ultrafiltered according to the procedure described in Example B-1. A $[\alpha]_D^{25}$ of −2.55° showed that the sample was enriched in (L)-tryptophan [enantiomeric excess of (L)-tryptophan ∼17 percent].

4. An aqueous solution of the copolymer of Example 3 (4.50 g of 15.7 weight percent solution) was added to the solution of racemic (D,L)-tryptophan (100 mg) in 0.01M HCl (1.50 g). The resulting clear mixture was ultrafiltered according to the procedure described in Example B-1. A $[\alpha]_D^{25}$ of −2.16° showed that the sample was enriched in (L)-tryptophan [enantiomeric excess of (L)-tryptophan ∼15 percent].

What is claimed is:

1. An optically-active, amphiphilic, water-soluble free-radical addition copolymer of ethylenically unsaturated monomers which comprises:
    a) a hydrophobic component having a chiral moiety; and
    b) a hydrophilic component having an anionic sulfonate group or a cationic sulfonium group.

2. The copolymer of claim 1 which comprises:
    (a) 25–80 weight percent of a hydrophilic component having an anionic sulfonate functionality or a cationic sulfonium functionality;
    (b) 3–70 weight percent of a hydrophobic component having a chiral functionality; and
    (c) 0–62 weight percent of an achiral hydrophobic component.

3. The copolymer of claim 2 having a cationic sulfonium functionality.

4. The copolymer of claim 2 having an anionic sulfonate functionality.

5. The copolymer of claim 2 which comprises:
    (a) 30–60 weight percent of a hydrophilic component having an ionic sulfonate or sulfonium functionality;
    (b) 10–50 weight percent of a hydrophobic component having a chiral functionality; and
    (c) 15–55 weight percent of an achiral hydrophobic compent.

* * * * *

UNITED STATES PATENT AND TRADEMARK OFFICE
CERTIFICATE OF CORRECTION

PATENT NO. : 5,391,634
DATED : February 21, 1995
INVENTOR(S) : Mladen Ladika and Thomas E. Fisk It is certified that error appears in the above-indentified patent and that said Letters Patent is hereby corrected as shown below:

Column 12, line 67, "compent" should read --component--.

Signed and Sealed this

Thirtieth Day of April, 1996

Attest:

BRUCE LEHMAN

*Attesting Officer*    Commissioner of Patents and Trademarks